United States Patent [19]

Feinland et al.

[11] Patent Number: 4,529,404
[45] Date of Patent: Jul. 16, 1985

[54] HAIR DYE PREPARATION

[75] Inventors: Raymond Feinland, Stamford, Conn.; Sigmund Iscowitz, Flushing, N.Y.

[73] Assignee: Clairol Incorporated, New York, N.Y.

[21] Appl. No.: 413,185

[22] Filed: Aug. 30, 1982

Related U.S. Application Data

[63] Continuation of Ser. No. 116,738, Jan. 30, 1980, abandoned, which is a continuation of Ser. No. 950,345, Oct. 11, 1978, abandoned, which is a continuation of Ser. No. 701,440, Jun. 30, 1976, abandoned.

[51] Int. Cl.$^3$ ............................. A61K 9/12; D06P 3/04
[52] U.S. Cl. ............................................ 8/406; 8/407; 8/408; 8/410; 8/424; 424/47
[58] Field of Search ................... 8/406, 405, 408, 407, 8/410, 424; 424/47

[56] References Cited

U.S. PATENT DOCUMENTS

| 2,975,101 | 3/1961 | Charle et al. | 8/406 |
| 3,011,858 | 12/1961 | Lantz et al. | 8/405 |
| 3,488,138 | 1/1970 | Iscowitz | 8/406 |

FOREIGN PATENT DOCUMENTS

| 2501862 | 7/1975 | Fed. Rep. of Germany . | |
| 7500528 | 1/1975 | Sweden . | |
| 824519 | 12/1959 | United Kingdom . | |
| 995948 | 6/1965 | United Kingdom . | |
| 993923 | 6/1965 | United Kingdom . | |
| 1385058 | 2/1975 | United Kingdom . | |
| 1489344 | 10/1977 | United Kingdom | 8/406 |
| 1491980 | 11/1977 | United Kingdom . | |

OTHER PUBLICATIONS

Nature, 4/8/50, vol. 165, pp. 569–570.
Burton, J. Soc. Cos. Chem., 1951, vol. 2, pp. 240–244.
Burton et al., J.S.D.C., 1966, pp. 474–478.
Cilento et al., Biochim, Biophys Act, 1967, 143, pp. 89–92.

Primary Examiner—Dale R. Ore
Attorney, Agent, or Firm—Gabriel P. Katona

[57] ABSTRACT

An autoxidizable hair dye preparation is disclosed capable of coloring or darkening hair when applied thereto and exposed to the atmosphere comprising a mixture of (I) at least one p-phenylene diamine compound, or an acid addition salt thereof, and (II) at least one 1,2,4-benzenetriol compound, each compound optionally containing nuclearly substituted $C_{1-4}$ alkyl, alkoxy, hydroxyalkyl or halogen. The preparation is preferably applied and exposed to the atmosphere repeatedly until the desired degree of darkening or color build-up is attained.

14 Claims, No Drawings

HAIR DYE PREPARATION

This application is a continuation of Ser. No. 116,738, filed on Jan. 30, 1980 which is a continuation of Ser. No. 950,345 filed on Oct. 11, 1978, which is a continuation of Ser. No. 701,440, filed on June 30, 1976, all now abandoned.

This invention relates to compositions or preparations for coloring or darkening hair, and more particularly to such preparations containing a mixture of two certain types of compounds, and a method for their use.

It has long been known in the prior art that p-phenylene diamine and p-toluylene diamine are capable of coloring hair, but the coloring process is very slow unless applied in combination with an oxidizing agent such as hydrogen peroxide which must be kept apart from these diamines until immediately prior to use and which often damages the hair. It has also long been known in the prior art that benzenetriols such as 1,2,4-benzenetriol(4-hydroxy catechol, hydroxy quinol) and 2,4,5-trihydroxytoluene are likewise capable of coloring hair, but although the coloring process under atmospheric conditions is relatively rapid, it yields only relatively light shades.

Several references in the prior art refer to the use of the above compounds for coloring hair. In this connection, attention is invited to U.S. Pat. Nos. 2,162,458, 2,733,186, 2,975,101, 3,214,472, 3,236,734, and 3,920,384, and British Pat. Nos. 710,134, 745,532, 754,948, 754,949, 824,519, and 827,439. However, although some of these references, for example U.S. Pat. No. 2,162,458, British Pat. No. 710,134 and British Pat. No. 827,439, state that mixtures of certain p-phenylene diamine compounds and benzenetriol compounds were theretofore suggested for coloring hair, they fail to specifically disclose any such mixtures, implying that such mixtures were found to be unsatisfactory, perhaps with respect to coloring rate, depth of color, safety, drabness, permanence and/or facility in production or use or the like.

It is an object of this invention to provide hair coloring (including darkening) preparations which will not be subject to one or more of the above disadvantages.

Other objects and advantages will appear as the description proceeds.

The attainment of the above objects is made possible by this invention which includes the provision of an autoxidizable hair preparation capable of coloring (including darkening) hair when applied thereto and exposed to the atmosphere comprising a mixture of (I) at least one p-phenylene diamine compound or an acid addition salt thereof, and (II) at least one 1,2,4-benzenetriol compound, each compound optionally containing nuclearly substituted halogen or $C_{1-4}$ alkyl, alkoxy or hydroxyalkyl. The optional nuclear substituent is preferably methyl, and preferably in the 5-position in the benzenetriol compound.

The above-defined preparation of this invention, when applied to the hair, e.g. gray hair, at least once and preferably up to four or more times, with exposure to the atmosphere at ambient temperatures after each application, for example twice a day for two days, have been found to yield natural-looking, drab medium to dark brown colorations which are relatively durable and resistant to further color change when subsequently shampooed.

As illustrative of suitable compound (I) type compounds, there may be mentioned the 1,4-diamino-5-ethyl, -isobutyl -methoxy, -butoxy, -hydroxyethyl, -chloro, and -bromo benzenes, and preferably p-phenylene diamine (PPD, 1,4-diamino benzene, p-amino aniline), and p-toluylene diamine (PTD, 1,4-diamino-5-methyl benzene), and their acid addition salts (e.g. sulfate, chloride, bromide, etc.), and mixtures thereof.

As illustrative of suitable compound (II) type compounds, there may be mentioned the 1,2,4-trihydroxy-3-, -6-, 7- and preferably -5-ethyl, -isobutyl, -methoxy, -butoxy, -hydroxyethyl, -chloro, -bromo, and preferably -methyl benzenes, and especially 1,2,4-benzenetriol (Benz T, 4-hydroxy catechol, hydroxy hydroquinone), and 2,4,5-trihydroxy toluene (THT, 1,2,4-trihydroxy-5-methyl benzene, 4-hydroxy-5-methyl catechol), and mixtures thereof.

The molar ratio of compound (I) (or mixtures thereof) to compound (II) (or mixtures thereof) in the mixtures of this invention may range from about 1:8 to about 4:1, preferably about 1:2 to about 2:1, and the preparations of this invention may contain about 0.04 to about 8%, preferably about 0.1 to about 6%, by weight of such mixtures. Such preparations will usually contain about 0.02 to about 1.0% by weight of each of said compounds (I) and (II).

In view of the sensitivity of these mixtures and preparations to oxidation, the compound (II) type triols especially tending to oxidize rapidly, such mixtures and preparations should preferably be prepared, packaged and stored under anaerobic conditions. When packaged as an aerosol under pressure, the usual hydrocarbon or halohydrocarbon propellants therein effectively provide such anaerobic conditions. Free space in other containers for these mixtures and preparations may be eliminated, minimized or filled with nitrogen or other inert gas. Premature oxidation may be further reduced or eliminated by including in such preparations small amounts, such as about 0.03% to 5% by weight, of one or more antioxidants or reducing agents, for example sodium sulfite, sodium bisulfite, ascorbic acid, aliphatic mercaptans such as thioglycollic acid, thiolactic acid and thioglycerol and the like. Alternatively, the compound (II) type triol compounds may be protected from premature oxidation by acylation, e.g. as the triacetate, and the acylated compound saponified to the triol in known manner immediately prior to or concurrently with application of the preparation to the hair. In any case, it will be understood that the fluid vehicle in which the mixture is generally suspended, dispersed or dissolved usually provides an additional substantially anaerobic environment further tending to reduce premature oxidation of the dye mixtures of this invention until it is exposed to atmospheric oxygen in situ on the hair.

The preparations of this invention are generally fluid or liquid, in the form of a solution, dispersion, suspension, cream, lotion, gel or aerosol or the like, and optionally in combination with hair grooming or hair conditioning agents whereby the hair, whether it be live as on the head, or dead as in a swatch, wig or hairpiece, is simultaneously colored and groomed or conditioned. Water is ordinarily the major constituent or vehicle in the instant preparations, and may for example constitute from about 30 to about 95% by weight thereof. Alcohols such as ethanol, isopropyl alcohol, glycols, and derivatives thereof, ranging from about 0 to about 30% by weight in the preparations, may be included as mutual solvents or solubilizing agents. The pH of these preparations is ordinarily adjusted to about 4 to 11, preferably about 6 to 10, more preferably about 7 to 9, with acidic materials, buffers or alkalizing agents such as mono-, di- and tri-ethanolamine, sodium carbonate and bicarbonate, disodium hydrogen phosphate, sodium dihydrogen phosphate, and the like.

These preparations may also contain up to about 6% by weight of known couplers, which are aromatic compounds commonly employed to control or vary the hair color or shade, such as 2-4-diamino-phenol, -anisole and -toluene, m-methoxy- and -aminophenol, 2,5- and 2,6-xylenol, catechol, resorcinol, m-phenylene diamine, 3-amino-4-methyl and -6-methyl phenol, alpha-naphthol, 1-phenyl-3-methyl-5-pyrazolone and the like.

The preparations of this invention may also contain known additives or assistants such as hair grooming agents, for example quaternized vinyl pyrrolidone copolymers, carboxyvinyl polymers and the like, plasticizers, conditioners, thickeners, slip and wetting agents such as polyoxyethylenated fatty (e.g. lauryl) alcohols, stearyldimethylammonium chloride, silicone copolymer, foam boosters, preservatives, perfumes and the like. For packaging and dispensing as an aerosol, from about 5 to 50% or more by weight of a known propellant or mixture thereof may be included such as the hydrocarbons, e.g. propane and butane, and halohydrocarbons, e.g. Freons 12,114,152A, etc.

The hair is preferably first washed or shampooed before applying the present preparations. The application may be discontinuous, as for example when a streaking or other decorative effect is desired, or uniformly in which case a sufficient amount of the preparation is employed to thoroughly wet the hair. For a normal head of hair this for example would generally call for application of about 15 to 20 ml. of the preparation. The final color and/or depth of shade in any particular instance will for the most part depend upon the concentrations of the (I) and (II) type compounds in the preparation, the temperature and duration of exposure of the wetted hair to atmospheric oxygen, and the number of repeated applications, increases in all of which will generally yield an increased depth or intensity of color or shade. No shampooing or rinsing is required after application as in the case with the usual hair coloring products.

The following examples are only further illustrative of preferred embodiments of this invention. All amounts and proportions referred to herein and in the appended claims are by weight unless otherwise indicated. As employed herein, the following terms have the indicated meanings:

Gafquat 755: quaternized vinyl pyrrolidone copolymer, average M.W. over 1,000,000, relative viscosity (Ostwald-Fenske) 1.5-2.0 as an 0.1% solution in anhydrous SD40 ethanol, minimum 19% solids in a water vehicle; GAF Corporation.

Emulphor AM650: 1 mole isostearyl alcohol reacted with 10 moles ethylene oxide (E.O.), GAF Corporation.

Brij 35: 1 mole lauryl alcohol reacted with 23 moles E.O.; ICI America.

Silicone SF-1066: dimethyl polysiloxane/polyethylene oxide/polypropylene oxide copolymer, visc. 1200-1500 centistokes at 25° C., sp. gr. 1.04 at 20° C., General Electric Co.

Propellant 152a: 1,1-difluoroethane.

Propellant 114: 1,2-dichloro-1,1,2,2-tetrafluoroethane.

Propellant 12: dichlorodifluoromethane.

Carbopol 941: water soluble salt of a polymer of acrylic acid cross-linked with about 1% of a polyalkyl ether of sucrose having an average of 5.8 allyl groups per sucrose molecule, M.W. of the order of 1,000,000, described in U.S. Pat. No. 2,798,053, B. F. Goodrich Co.

EXAMPLE 1

| PPD (p-phenylene diamine) | 0.147% |
| --- | --- |
| Benz T (1,2,4-benzenetriol) | 0.171 |
| sodium sulfite | 0.030 |
| sodium erythorbate | 0.030 |
| triethanolamine | 3.000 |
| deionized water   q.s. to | 100.000 | pH adjusted to 8.0 with sulfuric acid.

The above preparation, preferably blended and maintained under anaerobic conditions, is applied four times (twice a day for 2 days) to gray hair, each time followed with color development by air oxidation, to yield a natural looking medium to dark drab brown shade.

EXAMPLE 2

The procedure of Example 1 is repeated, except for substitution of the Benz T by an equivalent amount of THT (2,4,5-trihydroxytoluene), with similar results.

EXAMPLE 3

| PTD (p-toluylenediamine) | 0.300% |
| --- | --- |
| Benz T | 0.171 |
| sodium sulfite | 0.030 |
| sodium erythorbate | 0.030 |
| triethanolamire | 3.000 |
| deionized water   q.s. to | 100.000 | pH adjusted to 8.0 with sulfuric acid.

This preparation applied as described in Example 1 yields similar results.

EXAMPLE 4

The procedure of Example 3 is repeated, except for substitution of the Benz T by an equivalent amount of THT, with similar results.

EXAMPLE 5—AEROSOL FOAM

A clear near colorless solution is produced by blending with the formulation of Example 1 (disregarding the water):

| ethyl alcohol (95%) | 23.000 |
| --- | --- |
| Gafquat 755 | 2.000 |
| Emulphor AM650 | 0.053 |
| perfume | 0.013 |
| stearyldimethylbenzylammonium chloride | 0.067 |
| Silicone SF-1066 | 0.053 |
| Brij 35 | 0.040 |
| Water   q.s. to | 100.000 |

To 94 g. of the above preparation, 6 g. of a 30/35/35 propellant blend of 152a/114/12 is added to obtain a quick breaking aerosol foam. Application to hair as in Example 1 yields similar results. Likewise, similar addition of the above materials to the formulations of Examples 2-4 and combining with the propellant mixture yields quick breaking aerosol foams which are applied to hair with like results.

EXAMPLE 6—GEL 10 g. of Carbopol 941 are dispersed in 750 g. of cold water while vigorously agitating and raising the temperature to about 40°-50° C. and cooling to room temperature. To the smooth dispersion are added with stirring 1.47 g. of PPD and 1.2 g. of sodium sulfite, then a solution of 0.13 g. of perfume in 0.4 g. of Brij 35, then 1.71 g. Benz T, and then 43 g. of triethanolamine. The pH of the resulting solution is adjusted to about 7.9-8.1 with triethanolamine and sulfuric acid, and water added to make 1,000 g. of a soft gel.

Hair is treated with the resulting gel as described in Example 1, with similar results. Substitution of the PPD by an equivalent amount of PTD, and/or of the Benz T by an equivalent amount of THT, yields similar results.

This invention has been disclosed with respect to certain preferred embodiments, and it will be understood that modifications and variations thereof obvious to those skilled in the art are to be included within the spirit and purview of this application and the scope of the appended claims.

What is claimed is:

1. An anaerobic autoxidizing preparation adapted to color or darken hair to form medium to dark shades when applied to hair without the use of any oxidizer other than exposure to the atmosphere, essentially consisting of an aqueous carrier, and (I) at least one aryldiamine of the formula

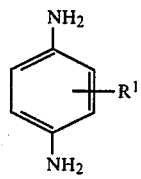

or an acid addition salt thereof, and
(II) at least one 4-hydroxy catechol compound of the formula

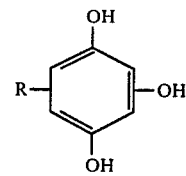

wherein $R^1$ and R are independently of each other hydrogen, halogen, or a $C_{1-4}$ alkyl, $C_{1-4}$ alkoxy, or $C_{1-4}$ hydroxyalkyl residue, the ratio of said compound I to said compound II being in the range of from about 1:8 to 4:1, compound I and compound II together comprising from about 0.04% to about 8% by weight of said composition.

2. A preparation according to claim 1 wherein R is in the 5-position.

3. A preparation according to claim 1 wherein $R^1$ and R are individually hydrogen or methyl.

4. A preparation according to claim 1 wherein $R^1$ and R are each hydrogen.

5. A preparation according to claim 1 wherein $R^1$ is hydrogen and R is methyl in the 5-position.

6. A preparation according to claim 1 wherein $R^1$ is methyl and R is hydrogen.

7. A preparation according to claim 1 wherein $R^1$ is methyl and R is methyl in the 5-position.

8. A preparation according to claim 1 wherein said mixture of (I) and (II) compounds comprises about 0.1 to about 6% by weight of the preparation.

9. A preparation according to claim 1 containing about 0.02 to about 1.0% by weight of each of said compounds (I) and (II).

10. A preparation according to claim 1 in the form of an aqueous solution.

11. A preparation according to claim 1 in the form of an aerosol composition also containing a propellant system.

12. A preparation according to claim 1 also including a hair grooming agent.

13. A method of coloring hair comprising applying to the hair an effective amount of a preparation according to claim 1.

14. A method according to claim 13 wherein the preparation is applied to the hair at multiple spaced intervals of time and permitted to be exposed to the atmosphere after each application whereby a gradual build-up of color is developed in said hair.

* * * * *